(12) United States Patent
Murakami

(10) Patent No.: US 10,675,181 B2
(45) Date of Patent: Jun. 9, 2020

(54) VITREOUS BODY CUTTER

(71) Applicant: MANI, Inc., Utsunomiya-shi, Tochigi (JP)

(72) Inventor: Etsuo Murakami, Utsunomiya (JP)

(73) Assignee: MANI, INC., Utsunomiya-shi, Tochigi (JP)

( * ) Notice: Subject to any disclaimer, the term of this patent is extended or adjusted under 35 U.S.C. 154(b) by 138 days.

(21) Appl. No.: 15/756,561

(22) PCT Filed: Sep. 1, 2016

(86) PCT No.: PCT/JP2016/075637
§ 371 (c)(1),
(2) Date: Feb. 28, 2018

(87) PCT Pub. No.: WO2017/038931
PCT Pub. Date: Mar. 9, 2017

(65) Prior Publication Data
US 2018/0243133 A1    Aug. 30, 2018

(30) Foreign Application Priority Data

Sep. 1, 2015 (JP) .................................. 2015-171766

(51) Int. Cl.
*A61F 9/007* (2006.01)

(52) U.S. Cl.
CPC .......... *A61F 9/00736* (2013.01); *A61F 9/007* (2013.01); *A61B 2217/005* (2013.01)

(58) Field of Classification Search
CPC .. A61F 9/007; A61F 9/00736; A61F 9/00754; A61F 9/00763; A61F 9/008;
(Continued)

(56) References Cited

U.S. PATENT DOCUMENTS

| 2008/0033462 A1* | 2/2008 | Di Nardo ................ A61F 9/007 606/166 |
| 2011/0152774 A1 | 6/2011 | Lopez et al. |

(Continued)

FOREIGN PATENT DOCUMENTS

| JP | H03133449 A | 6/1991 |
| JP | 2008043755 A | 2/2008 |

(Continued)

OTHER PUBLICATIONS

International Search Report (ISR) for Application No. PCT/JP2016/075637 dated Nov. 1, 2016.

(Continued)

*Primary Examiner* — Elizabeth Houston
*Assistant Examiner* — Mohamed G Gabr
(74) *Attorney, Agent, or Firm* — Isshiki International Law Office; Joseph P. Farrar, Esq.

(57) ABSTRACT

A vitreous body cutter that allows wide movement of an opening position at the end part of a pipe even when the pipe is thin and that allows suction of vitreous bodies etc. in a wide range. The vitreous body cutter includes: a pipe having an opening on the side of an end part; a cutter, which slides along the inner surface of the pipe; a power output section, which is connected to the pipe and slides the cutter; and an outer case, through which the pipe passes, and which includes the power output section inside; and further includes a joint for connecting the outer case to a cannula attached to an eyeball. The protrusion length of the pipe from the outer case can be changed.

1 Claim, 5 Drawing Sheets

(58) Field of Classification Search
CPC ....... A61F 2240/001; A61F 2250/0065; A61B 2217/005; A61B 17/3421; A61B 2017/00526; A61B 2017/3492; A61B 2090/036
See application file for complete search history.

(56) References Cited

U.S. PATENT DOCUMENTS

| | | |
|---|---|---|
| 2015/0223979 A1 | 8/2015 | Murakami |
| 2016/0067091 A1* | 3/2016 | Wells ................ A61F 9/00763 606/107 |

FOREIGN PATENT DOCUMENTS

| | | |
|---|---|---|
| JP | 2013515563 A | 5/2013 |
| JP | 2014042703 A | 3/2014 |

OTHER PUBLICATIONS

Translation of the ISR for Application No. PCT/JP2016/075637 dated Nov. 1, 2016.
Written Opinion of the International Search Authority for Application No. PCT/JP2016/075637 dated Nov. 1, 2016.

\* cited by examiner (a)

(b)

(a)

(b)

(a)

(b)

VITREOUS BODY CUTTER

TECHNICAL FIELD

The present invention relates to a vitreous body cutter used in ophthalmic surgery.

BACKGROUND ART

The vitreous body cutter used in ophthalmic surgery is used for cutting and removing from an eyeball a jelly-like vitreous body and/or a proliferative membrane (called "vitreous body etc." hereafter) on the retina which is generated through denaturation of the vitreous body. Patent Document 1 discloses a structure of the end part of such a vitreous body cutter (vitreous body surgical probe). FIG. 5 is a cross-sectional view of the end part of the vitreous body cutter.

The vitreous body cutter includes a pipe 20 whose end part is sealed, and a cutter 30, which is slidable in the axial direction of the pipe 20 on the inner surface thereof with continuous contact on that surface. An opening 21 is formed in the side near the tip of the pipe 20, and the vitreous bodies etc. 65 are sucked in through the opening. At this time, the cutter 30 slides on the inner surface of the pipe 20, and when the tip of the cutter 30 passes by the opening 21, the vitreous bodies etc. 65 are cut off. The vitreous bodies etc. 65 cut smaller are sucked in at the back side of the pipe 20 (on the right side of FIG. 5).

Such a vitreous body cutter is used by being put into a cannula or pipe inserted into the eyeball. When the diameter of the pipe of the vitreous body cutter is small, it is difficult to move the opening position widely within the eyeball because the pipe may be bent on the outside of the cannula when trying to move the opening position at the end part of the pipe. However, since the vitreous body cutter is used for operation within the eyeball, the smallest possible pipe diameter is preferred. A 27 gauge pipe (0.4 mm) is often used these days, and such a thin vitreous body cutter has particularly low rigidity. Therefore, an operation without eyeball movement is strongly recommended.

However, when it is hard to move the pipe widely and without eyeball movement, the range of sucking in the vitreous bodies etc. is restricted. As a result, there is a greater possibility that residual vitreous bodies etc. will remain in the eyeball. Therefore, even in the case where the pipe of the vitreous body cutter is thin, an operation while moving the vitreous body cutter and the eyeball freely is desired.

PRIOR ART DOCUMENTS

Patent Documents

[Patent Document 1] JP 2014-42703A

DISCLOSURE OF INVENTION

Problem to be Solved by the Invention

In view of this problem, the present invention aims to provide a vitreous body cutter that allows wide movement of an opening position in the end part of a pipe even when the pipe is thin and that allows suction of vitreous bodies in a wide range.

Solution to the Problem

The vitreous body cutter according to the present invention includes a pipe with an opening on the side of an end part; a cutter, which slides along the inner surface of the pipe; a power output section, which is connected to the pipe and slides the cutter; and an outer case, through which the pipe passes, and which comprises the power output section inside; and further includes a joint for connecting the outer case to a cannula attached to an eyeball.

Moreover, it is preferable that the pipe, the cutter, and the power output section can shift along the axis of the pipe relative to the outer case, and the protrusion length of the pipe from the outer case can be changed.

Advantageous Effect of the Invention

Since a vitreous body cutter and a cannula are unified to be a single body according to the present invention, the following effect is provided: the range in which the opening of a pipe can be moved within an eyeball is wide even when the pipe is thin, and range in which the vitreous body can be sucked in is wide.

Moreover, since the protrusion length of the pipe from an outer case can be changed as desired, the following effect is provided: sucking in the vitreous bodies etc. in the front side of an eyeball is possible with a cannula unified with the vitreous body cutter.

DESCRIPTION OF EMBODIMENTS

An embodiment according to the present invention is described below with reference to accompanying drawings.

Figure 1:
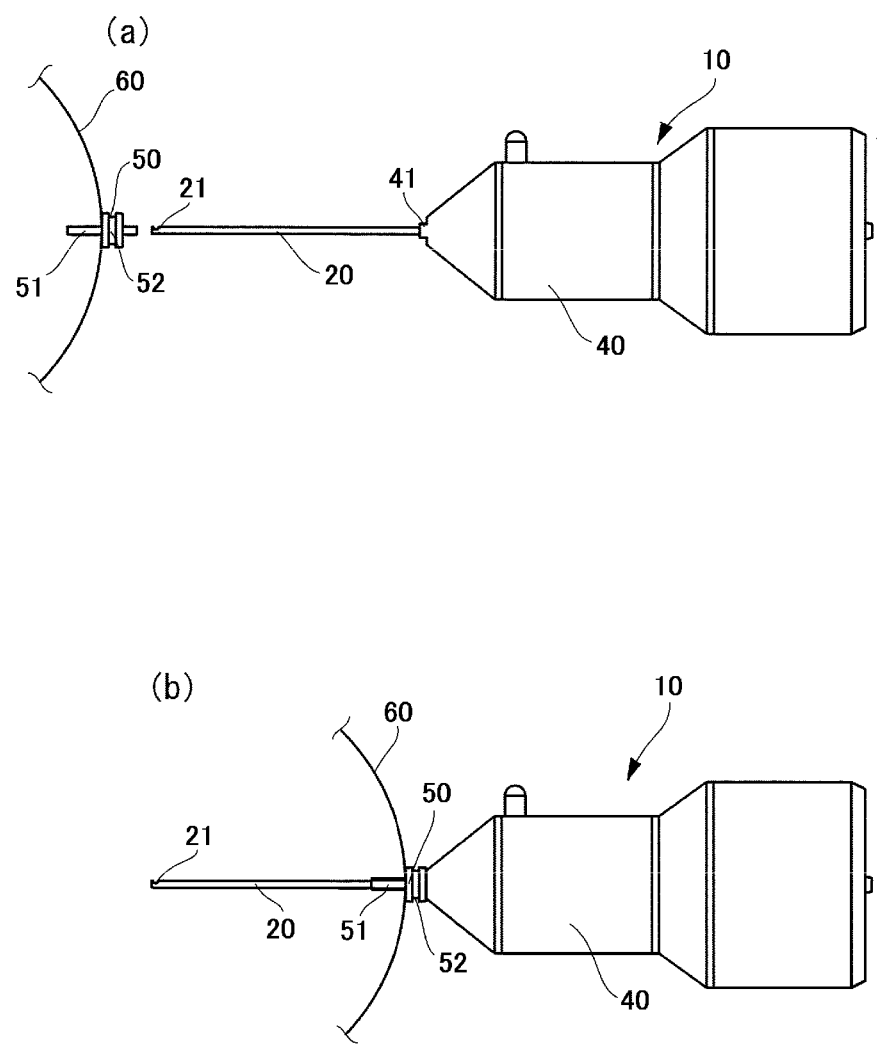
FIG. 1 shows outlines of a vitreous body cutter according to the present invention; wherein (a) shows the vitreous body cutter before connected to a cannula, and (b) shows the vitreous body cutter after connected to the cannula.

FIG. 1 shows outlines of a vitreous body cutter according to the present invention; wherein FIG. 1(a) shows the vitreous body cutter before connected to a cannula, and FIG. 1(b) shows the vitreous body cutter after connected to the cannula. A vitreous body cutter 10 sucks in vitreous bodies etc. from an eyeball 60 by inserting a pipe 20 of the vitreous body cutter 10 into a cannula 50 inserted into the eyeball 60.

The vitreous body cutter 10 has an outer case 40 through which the pipe 20 protrudes. The tip of the pipe 20 is sealed. An opening 21 for sucking in the vitreous bodies etc. is formed in a side of the end part. A power output section that is connected to the pipe 20 is built in the outer case 40. This power output section slides the cutter 30 along the inner surface of the pipe 20. The vitreous bodies etc. are removed in the same way as described above; namely, when the cutter 30 slides along the inner surface of the pipe 20, the vitreous bodies etc. sucked in through the opening 21 are cut smaller, and then sucked further into the depth of the pipe 20.

The cannula 50 includes a tubular main body 51, which is inserted into the eyeball 60, and a base 52, which serves as a stopper. As shown in FIG. 1(a), the pipe 20 of the vitreous body cutter 10 is put in the main body 51 of the cannula 50 attached to the eyeball 60, resulting in the state shown in FIG. 1(b). At this time, when a convex joint 41 prepared on the outer case 40 is connected to the base 52 of the cannula 50, the vitreous body cutter 10 and the cannula 50 are unified. Note that to the method of connecting the outer case 40 to the cannula 50 is not limited in particular, but they should be connected in such a manner that allows integrated movement of the cannula 50 and the pipe 20 when the outer case 40 is moved while they are connected.

Figure 2:
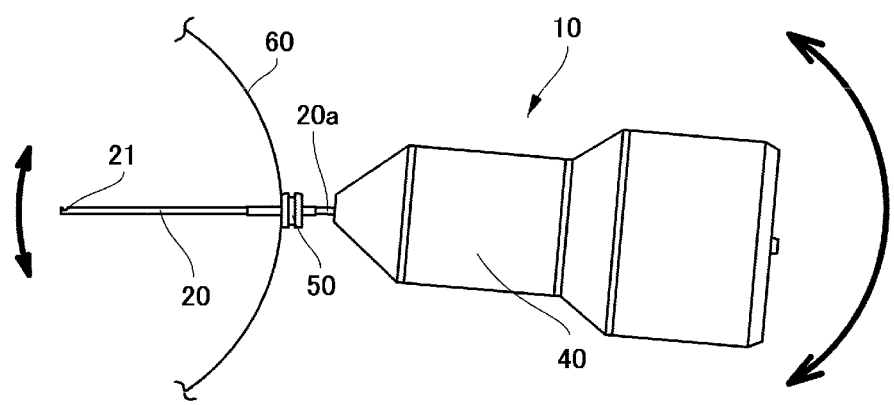
FIG. 2 shows moving ranges of the opening in the case where a pipe is thin; wherein (a) shows a conventional vitreous body cutter, and (b) shows a vitreous body cutter according to the present invention.
Figure 2:
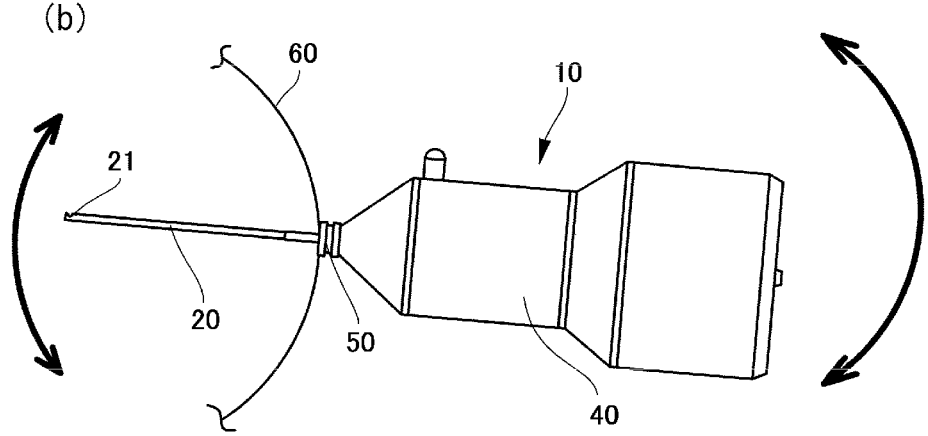

A result from unifying the vitreous body cutter 10 with the cannula 50 in such a manner is described below. FIG. 2 shows a moving range of the opening in the case where the pipe is thin; FIG. 2(a) shows a conventional vitreous body cutter, and FIG. 2(b) shows a vitreous body cutter according to the present invention.

In FIG. 2(a), since the vitreous body cutter 10 and the cannula 50 are not unified, and the pipe 20 is thin, the pipe 20 will bend at a position 20a outside the cannula 50 when the outer case 40 is moved. This makes it difficult to move the pipe 20 widely within an eyeball.

Therefore, unifying the vitreous body cutter 10 and the cannula 50 in such a manner as shown in FIG. 2(b) allows movement of the cannula 50 and the pipe 20 at the same angle as that of the outer case 40 when the outer case 40 is moved. As a result, the opening 21 provided in the end part of the pipe 20 can be widely moved.

However, in the case where the vitreous body cutter 10 and the cannula 50 are unified, backward and forward movement of the outer case 40 (in the direction of moving close to and away from an eyeball) is restricted, so as to prevent the cannula 50 from detaching from the eyeball 60. As a result, movement of the opening 21 will be allowed only at a fixed depth of the eyeball 60. Therefore, in order to make it possible to change the insertion depth, we have decided to enable adjustment of the protrusion length of the pipe 20.

Figure 3:
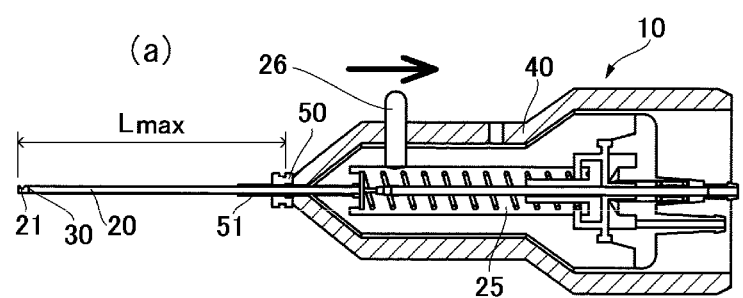
FIG. 3 shows cross-sectional views of the internal structure of the vitreous body cutter according to the present invention; wherein (a) shows the case where the protrusion length of the pipe is large, and (b) shows the case where the protrusion length of the pipe is small.
Figure 3:
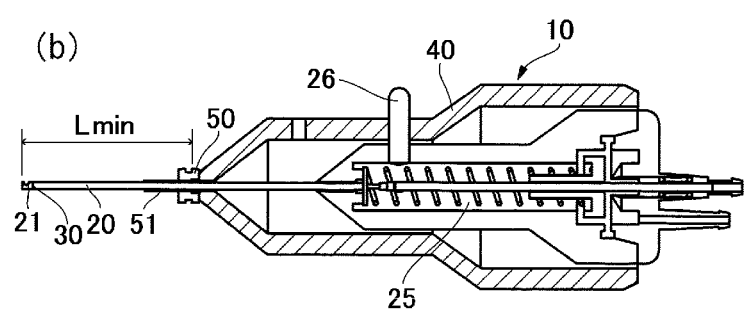

FIG. 3 show cross-sectional views of an internal structure of the vitreous body cutter according to the present invention; wherein FIG. 3(a) shows the case where the protrusion length of the pipe is large, and FIG. 3(b) shows the case where the protrusion length of the pipe is small. The state where the cannula 50 and the vitreous body cutter 10 are unified is illustrated in the drawings. As for a protrusion length L from the outer case 40, FIGS. 3(a) and 3(b) exemplify the maximum protrusion length Lmax and the minimum protrusion length Lmin, respectively.

Since the pipe 20, the cutter 30, and the power output section 25 are combined to be a single body, adjustment of the protrusion length L can be made by shifting the power output section 25 built in the outer case 40 backward and/or forward relative to the outer case 40.

How to move the power output section 25 is not limited in particular. In the example shown in FIG. 3, however, a protrusion length adjustor 26 connected to the power output section 25 is penetrated through the outer case 40, and the protrusion length L is changed by sliding the protrusion length adjustor 26 along the axis of the pipe 20.

Figure 4:
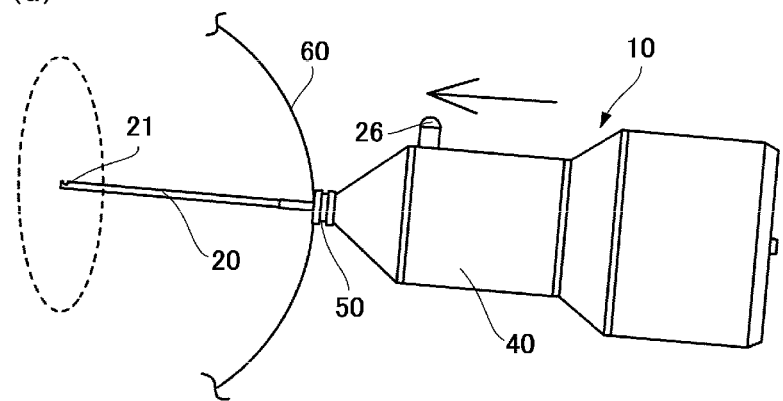
FIG. 4 shows the moving ranges of the opening according to the present invention; wherein (a) shows the case where the protrusion length of the pipe is small, and (b) shows the protrusion length of the pipe is large.
Figure 4:
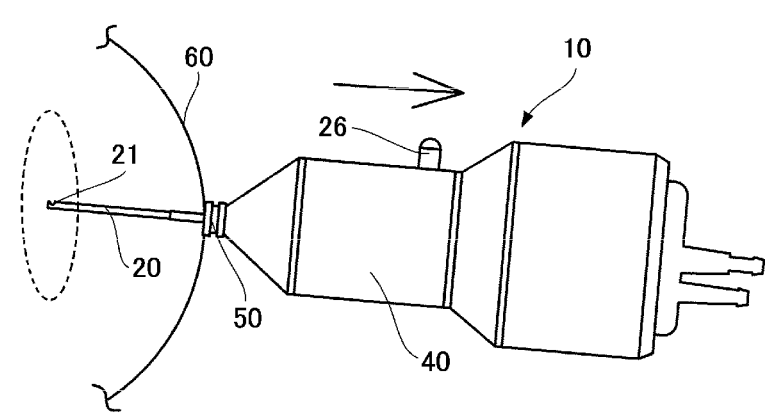
Figure 5:
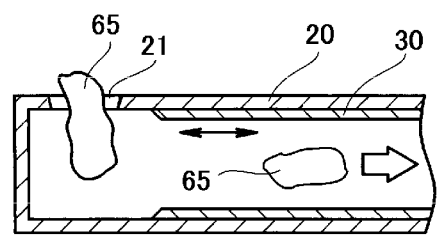
FIG. 5 is a cross-sectional view of an end part of the vitreous body cutter.

FIG. 4 shows moving ranges of the opening according to the present invention; wherein FIG. 4(a) shows the case where the protrusion length of the pipe is large, and FIG. 4(b) shows the case where the protrusion length of the pipe is small. Dashed lines denote the moving ranges of the opening 21.

When the protrusion length is large, the vitreous body etc. located deep in the eyeball 60 can be sucked in, as shown in FIG. 4(a). If the cannula 50 and the vitreous body cutter 10 are unified but the protrusion length of the pipe 20 cannot be changed, it is difficult to suck in the vitreous body etc. located in the front side of the eyeball 60 without extracting the cannula 50 from the eyeball 60. Meanwhile, according to the present invention, the protrusion length of the pipe 20 can be changed. Therefore, making a protrusion length smaller enables the vitreous body etc. located in the front side of the eyeball 60 to be sucked in without extracting the cannula 50 from the eyeball 60.

According to the present invention, the cannula and the vitreous body cutter are unified as described above, thereby allowing the opening to be shifted widely even when the pipe is thin. Furthermore, the vitreous bodies etc. in the entire eyeball can be sucked in by making it possible to change the protrusion length of the pipe.

EXPLANATION OF REFERENCES

10: Vitreous body cutter
20: Pipe
21: Opening
25: Power output section
26: Protrusion length adjustor
30: Cutter
40: Outer case
41: Joint
50: Cannula
51: Main body
52: Base
60: Eyeball
65: Vitreous body etc.

The invention claimed is:
1. A vitreous body cutter comprising:
a pipe comprising an opening at one terminal end thereof,
a cutter, which slides along an inner surface of the pipe,
a power output section, which is connected to the pipe and slides the cutter, and
an outer case, through which the pipe passes, and which comprises the power output section inside;
further comprising a joint for connecting the outer case to a cannula attached to an eyeball,
wherein the pipe, the cutter, and the power output section can shift along the longitudinal axis of the pipe relative to the outer case, and a protrusion length of the pipe from the outer case can be changed.

* * * * *